United States Patent [19]

Alvarez et al.

[11] Patent Number: 5,130,327
[45] Date of Patent: Jul. 14, 1992

[54] INDOLE DERIVATIVES

[75] Inventors: Eldiberto F. Alvarez; Carlos E. Recalde; Maria Angeles C. Villalobos; Antonio Diaz Diaz; Carlos B. Barrios; Maria del Carmen O. Estomba, all of Madrid, Spain

[73] Assignee: Consejo Superior De Investigaciones Cientificas, Madrid, Spain

[21] Appl. No.: 585,137

[22] PCT Filed: Feb. 8, 1990

[86] PCT No.: PCT/EP90/00221
  § 371 Date: Oct. 2, 1990
  § 102(e) Date: Oct. 2, 1990

[87] PCT Pub. No.: WO90/09375
  PCT Pub. Date: Aug. 23, 1990

[30] Foreign Application Priority Data

Feb. 8, 1989 [ES] Spain .................... 8900452

[51] Int. Cl.$^5$ .................... A61K 31/405; C07D 209/16
[52] U.S. Cl. .................... 514/415; 548/504
[58] Field of Search .................... 548/504; 514/415

[56] References Cited

PUBLICATIONS

Chem Abs., vol. 106, 1987, abstract 32831v, Alvarez et al., p. 529.
Chem Abs., vol. 111, 1989, abstract 133987j, Alvarez et al., p. 744.
J. Med. Chem., vol. 16, 1973, pp. 923–930, Fujita.

Primary Examiner—Mary C. Lee
Assistant Examiner—Joseph K. McKane
Attorney, Agent, or Firm—Stuart R. Suter; Edward T. Lentz

[57] ABSTRACT

Compounds of structure (1);

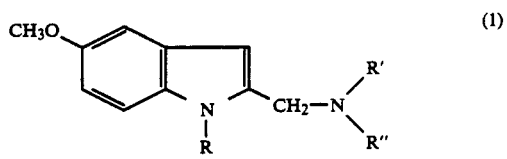

and pharmaceutically acceptable salts are described, where
  R is hydrogen or $C_{1-4}$alkyl,
  R' is hydrogen, $C_{1-4}$alkyl, or a $C_{1-4}$alkyl group substituted by an alkyne or allene group provided that R' is not methyl when R and R" are both hydrogen, and
  R" is hydrogen or a $C_{1-4}$alkyl group substituted by an alkyne or allene group.

These compounds have anti-depressant activity. Processes for the preparation of the compounds, pharmaceutical compositions and methods of use, are described.

13 Claims, No Drawings

INDOLE DERIVATIVES

The present invention relates to 2-aminomethyl-5-methoxyindole derivatives, processes for their preparation, their use as therapeutic agents and pharmaceutical compositions containing them. The compounds of this invention are of use in treating depression and medical conditions which are characterised by depletion of biogenic amines in the brain.

The enzyme monoamine oxidase [MAO, EC 1.4.3.4.] catalyses the oxidative deamination of important neuronal monoamines, including catecholamines and 5-hydroxytryptamine (5-HT, serotonin). The enzyme is currently known in two forms MAO-A and MAO-B which are characterised by different selectivities with regard to inhibitors and substrates. 5-HT, adrenaline and noradrenaline are preferentially metabolised by MAO-A, whereas benzylamine and β-phenethylamine are predominantly metabolised by MAO-B, and tyramine is a common substrate for both forms. Dostert P.L. et al., Med. Res. Rev. 9, 45–89 (1989).

The clinical usefulness of MAO inhibitors has been limited by the "cheese effect" (a hypertensive response to tyramine and other pressor amines present in some foodstuffs) and compounds which have good pharmacological activity and a weak "cheese effect" are of particular interest. Currently the inhibition of MAO-A is thought to give rise to anti-depressant effects, whereas the selective MAO-B inhibitor l-deprenyl is used in combination with L-Dopa in the treatment of Parkinsonism.

Although many inhibitors of MAO are known, the 1989 review by Dostert et al. concluded that "no simple patterns have yet emerged which will allow the rational design of potent MAO inhibitors with predictable selectivity."

In Spanish Patent 407,703 and Spanish Patents 421,185 and 421,186 we described 3-aminomethylindole and 3-(2-aminoethyl)indole derivatives. In Spanish Patent 542,696 and Application 8602588 we described 2-aminomethylindoles which do not have methoxy substituents. All these compounds are characterised as having alkyne or allene groups.

G. Bertaccini and P. Zamboni, Arch. Int. Pharmacodyn. 1961] 133 138–158, tested aminoalkylindole derivatives for 5-hydroxytryptamine-like activity on the rat uterus and the authors noted that "none of the examined compounds had marked antagonistic activity". 5-Methoxy-2-(methylaminomethyl)-indole (Compound It herein) was described as compound 48 and was one of five compounds referred to as "a weak unspecific antagonistic activity was also noted in some compounds bearing the side chain at the 2 position." The authors' views on structure-activity relationships included: "substitution of the hydroxy group at the 5-position of the indole ring with a methoxy group ( . . . ) brought about a tenfold reduction in activity", "shifting of the side chain from 3 to 2 position produced a strong decrease in biological activity of the tryptamines", "the effect of alkyl substitution in the amino nitrogen was variable", and "indolealkylamines with a single carbon atom lateral chain (gramine derivative) showed a negligible activity."

According to the present invention there is described 2-aminomethyl-5-methoxyindole compounds of structure (1):

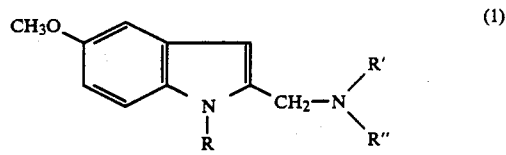

and pharmaceutically acceptable salts thereof, wherein
R is hydrogen or $C_{1-4}$alkyl,
R' is hydrogen, $C_{1-4}$alkyl, or a $C_{1-4}$alkyl group substituted by an alkyne or allene group, provided that R' is not methyl when R and R" are both hydrogen, and
R" is hydrogen or a $C_{1-4}$alkyl group substituted by an alkyne or allene group.

Suitably R is hydrogen or methyl.
Suitably R' is propargyl, 2-butynyl, 2,3-butadienyl or hydrogen or methyl.
Suitably R" is hydrogen, propargyl, 2-butynyl or 2,3-butadienyl.
Preferably R is methyl.
Preferably R' is methyl or R' and R" are both hydrogen.
Preferably R" is propargyl or 2-butynyl.
Specific preferred compounds of this invention are:

N-methyl-N-propargyl-2-[1-methyl-5-methoxyindolyl]-methylamine
N-propargyl-2-[1-methyl-5-methoxyindolyl]methylamine
N-(2-butynyl)-2-[1-methyl-5-methoxyindolyl]methylamine
N-(2-butynyl)-N-methyl-2-[1-methyl-5-methoxyindolyl]methylamine
N-(2,3-butadienyl)-2-[1-methyl-5-methoxyindolyl]methylamine
N-(2,3-butadienyl)-N-methyl-2-[1-methyl-5-methoxyindolyl]methylamine, and
5-methoxyindol-2-ylmethylamine and pharmaceutically acceptable acid addition salts thereof.

Compounds of structure (1) can form pharmaceutically acceptable acid addition salts with suitable organic and inorganic acids, the nature of which will be apparent to persons skilled in the art. For example, pharmaceutically acceptable salts can be formed by reaction with hydrochloric, sulphuric, sulphonic or phosphonic acids, or aliphatic, alicyclic, aromatic or heterocyclic carboxyl or sulphonic acids.

The compounds of structure (1) and their pharmaceutically acceptable salts are useful in the treatment of depression and in the treatment of conditions (anxiety, panic disorder, etc.) which are characterised by reduced levels of biogenic amines in the brain. The metabolic consequences of the MAO inhibition are: with regard to catecholamine metabolism they cause accumulation of neuronal mediators (dopamine, noradrenaline, etc.) thus giving rise to an adrenergic stimulant effect; with regard to 5-HT metabolism, they cause 5-HT accumulation which cannot be converted into 5-hydroxyindoleacetic acid and therefore, they have a serotonergic stimulant effect; with regard to tyramine metabolism, MAO inhibition causes it to be converted into octopamine which can operate as a false neurotransmitter.

The main indication of these MAO inhibitors is for the treatment of depression. They constitute a therapeutic class with a specific action, different to tricyclic antidepressants. They are very effective for panic attacks, atypical depressions (phobias, anxieties, neuroses) and recurrent depressions of the senile (absence of anticholinergic effects). Other specific indications of these MAO inhibitors are on psychasthenia characterized by fatigue without a physical reason (anergia), concentration difficulties, visceral symptoms and the narcolepsy-catalepsy syndrome.

The biochemical and pharmacological profiles of the compounds of structure (1) were determined.

To determine MAO inhibitory activity at the biochemical level the following tests are used:

1. "In vitro inhibition" of rat cerebral MAO A and B giving $I_{50}$ values for the two forms of the enzyme. Male Wistar rats (200 g) were used. Brains were obtained by decapitation and were homogenized. As substrates of the enzymes $^{14}$C-5-hydroxytryptamine oxalate 54 mCi/mmol and $^{14}$C-$\beta$-phenylethylamine were used. The residual enzymatic activities were referred to the activities in absence of MAO inhibitor (100%).

2. "Ex vivo inhibition" of rat cerebral MAO A and B after single dosing.

This gives the degree of inhibition in vivo of both forms of the enzyme and variation of this inhibition with time after treatment with a single dose. The compounds were administered intraperitoneally to male Wistar rats (175 g.) at a dose of 5 mg/kg in 1 ml/kg ($H_2O$). Animals were sacrificed by decapitation 24 h. and 7 days after treatment and brains were removed and homogenized. Enzymatic activities determined in treated animals, were compared with the activities in control animals (100%).

3. "Ex vivo" inhibition of rat cerebral MAO A and B after repeated dosing.

Male Wistar rats (175 g) were used.

The compounds were administered once daily intraperitonally for 7 days at a dose of 0.5 and 1 mg/kg in 1 ml/kg ($H_2$). One hour after the 7th dose, the animals were sacrificed and brains were removed to study MAO A and B activities as previously explained.

4. "In vivo" inhibition of MAO A and B of different tissues after chronic treatment.

In order to evaluate the effect of compounds in a chronic treatment, the inhibitory activity on brain, duodenum and liver MAO A and B has been studied "in vivo". Wistar male rats were treated at two dose levels, 0.1 and 0.25 mg/kg i.p. for 15 and 21 days. Control rats received similar amounts of saline solution.

Influence on the reuptake of monoamines "in vitro" was also studied. The effect of the compounds on the reuptake of 5-HT noradrenaline and dopamine was studied using Wistar male rats (350±2.5 g). They were kept under controlled light and temperature conditions and fed "ad libitum" until killed. The animals were killed by decapitation and brains were frozen and stored at −20° C. prior to analysis. Brains were dissected on an ice-filled petri dish. The cortices for 5-HT and noradrenaline assay and striatum (including caudate nucleus, putamen and globus pallidus) for dopamine assay were immediately weighed and homogenized. The standard incubation medium contained: 1.7 $\mu$M $^{14}$C-5-HT); 0.5$\mu$M $^3$H-noradrenaline or 1 $\mu$M $^3$H-dopamine with 0.1 ml of the crude synaptosomal preparation. All drugs used in the study were dissolved in the incubation medium in a concentration range $10^{-4}$ to $10^{-8}$ M and were preincubated with the crude synaptosomal preparation obtained from the treated brains, for 5 min. at 37° C. or 0° C. before the addition of the labelled substrate.

Effects of chronic treatment on $\alpha_2$-, $\beta$- and 5-$HT_2$ receptors. The test compounds, at a dose of 10 mg/kg/day i.p., were administered for 21 days to Wistar male rats (250±2.4 g). After treatment the animals were killed, brains were dissected and cortices were scraped from the dorsal surface of the cerebellum. $^3$H UK 14304, $^3$H Dihydroalprenalol and $^3$H Ketanserin were used as ligands in the binding studies.

The pharmacological profile was carried out assessing the antidepressant activity with the following tests:

Behavioural Despair (Porsolt et al. Arch. Int. Pharmacodyn; 229:327–336, 1977),

Learned Helplessness (Rubio P. et al. Pharmacol. Res. Comm. 20:141–143, 1988) and Olfactory Bulbectomy (O'Connor, W.T. et al. Prog. Neuropsycohopharmac. Biol. Psychiat., 12:41, 1988).

The action mechanism was studied in acute and chronic treatments on the interaction response with clonidine, salbutamol (Richard, J. Intern. J. Neuroscience, 9:17–19, 1979) and tetrabenazine (Pletscher, A.: An. N.Y. Aca. Sci. 80:1039–1045, 1959), and the response to the potentiation with L-dopa, L-tryptophan, tryptamine (Jalfre, M. et al., Arch. Int. Pharmacodyn, 159:194–221, 1982) and $\beta$-phenylethylamine (Ortmann, et al, Psychopharmacol. 84:22–27, 1984).

The secondary effects were studied mainly on the cardiovascular system, and the effects on the arterial pressure, heart rate and rhythm, P-R interval and isolated organ (rabbit aortic rings and isolated atria), were evaluated both after acute and chronic treatments. In the same way, the "cheese effect" was studied by means of the tyramine potentiation.

At a general pharmacological level the action of these products was studied on the following effects: anticholinergic, antihistaminic, spasmolytic, $\alpha_1$ agonist, anticonvulsant, antiparkinson, sedative, myorelaxing, hypnotic, anoretic, stimulant, hypothermic, intestinal motility and exploratory.

Compounds of structure (1) in which R" is an alkyl group substituted by an alkyne or allene group are potent MAO inhibitors with a selectivity for the type A enzyme; such inhibition is generally irreversible. In particular they have especially good activity when tested in in vivo experimental models, and in this regard they differ substantially from the corresponding 5-hydroxy and benzyloxy derivatives.

In particular, the compound "11" is an irreversible and selective inhibitor of MAO A. Its inhibitory effect is reached soon after the administration of a single dose (1 mg/kg) and it is observed even after 7 days when the dose administered is increased (5 mg/kg). The inhibitory effect with respect to MAO A is selective and is higher on cerebral MAO A than on intestinal or hepatic MAO A, without any effect on intestinal MAO B and a very low activity on hepatic MAO B. It is a potent inhibitor of the reuptake of 5-HT, a very weak inhibitor of the reuptake of dopamine and has no effect on the reuptake of noradrenaline.

The potency of the compound as inhibitor of 5-HT reuptake is much higher than that of chlorimipramine or imipramine (tricyclic antidepressants). The potency as inhibitor of dopamine reuptake is similar to that of amitryptiline and ten fold that of imipramine. Chronic administration of the compound in the rat, does not modify the number or the affinity of cerebral $\beta$-adrenergic receptors. The modifications observed on α-adrenergic and 5-HT receptors were not statistically significant.

In Porsolt's test, (1l) was much more active after chronic treatment than after acute treatment (MED, acute=50 mg/kg; MED, chronic=20 mg/kg). This fact allows us to confirm that the activity persists for at least 24 hours and the action mechanism is due to its irreversible character. In the specific tests for antidepressant activity, the compound "1l" appears to be active on Learned Helplessness (<10 mg/kg) and on Olfactory Bulbectomy (<5 mg/kg).

In the same way, in chronic treatment (1l) antagonized the hypoactivity reduced by clonidine (5 days) and salbutamol (14 days), not modifying it in acute treatment. The effects induced by tetrabenazine (ptosis and catalepsy) at 60 and 120 minutes after administration ($ED_{50} < 6$ mg/kg) were antagonized. The potentiation studies of (1l) on the effects produced by the biogenic amine precursors L-tryptophan, L-dopa and tryptamine confirm the MAO inhibitory activity. Similar results are obtained with 5-HT ($ED_{50} = 0.34$ mg/kg) and β-phenylethylamine ($ED_{50} = 27$ mg/kg).

The compound (1l) shows some "cheese effect" and it behaves as a hypotensive and negative chronotrope after both acute and chronic treatments.

Compounds of structure (1) in which R'' is hydrogen are inhibitors of MAO with little selectivity between the A and B forms. Of particular interest is the fact that these compounds show especially good activity when tested in in vivo experimental models. The MAO inhibition was generally reversible and the compounds were relatively non-toxic in rodents, and showed minimal cardiovascular effects. In addition, the compounds did not show a significant "cheese effect" which is a serious side-effect which limits the use of many MAOIs.

In particular the compound "1s" is a reversible and mixed inhibitor of MAO. It does not affect the reuptake of noradrenaline. Chronic administration of the compound "1s" does not modify the number or the affinity cerebral β-adrenergic receptors. In the specific pharmacological tests for antidepressant activity (1s) appeared to be active on Porsolt's test (MED=25 mg/kg. acute), Learned helplessness (<10 mg/kg. acute) and on Olfactory Bulbectomy (<10 mg/kg), counteracting some of the behavioural deficits of the Olfactory Bulbectomized rats. The compound "1s" had no action on clonidine-induced hypoactivity after acute (10.2 mg/kg.) and chronic treatment (10.2 mg/kg) during 5 days. However, it counteracts the hypoactivity induced by salbutamol in chronic treatment (10.2 mg/kg), but does not do so in the acute treatment. It appeared inactive in the tests of potentiation of β-phenylethylamine and 5-HT. In addition it does not produce any significant cardiovascular effects and has no "cheese effect".

In therapeutic use, the compounds of the present invention will usually be administered in a standard pharmaceutical composition.

The present invention also provides in a further aspect pharmaceutical compositions comprising a compound of structure (1) or a pharmaceutically acceptable salt thereof and a pharmaceutically acceptable carrier.

The compounds of structure (1) and their pharmaceutically acceptable salts which are active when given orally can be formulated as liquids, for example syrups, suspensions or emulsions, tablets, capsules and lozenges. A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of formula (1) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of the formula (1) or a pharmaceutically acceptable salt thereof calculated as the free acid.

The present invention also provides a method of combatting depression and medical conditions characterised by depleted levels of biogenic amines in the brain which comprises administering to a mammal in need thereof an effective amount of a compound of the formula (1) or a pharmaceutically acceptable salt thereof. The daily dosage regimen for an adult human may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the formula (1) or a pharmaceutically acceptable salt thereof calculated as the free base, the compound being administered 1 to 4 times per day. Suitably the compounds will be administered for a period of continuous therapy, for example for a week, several months or more. The dosage levels and frequency can be varied over the period and generally the dosage will be reduced before treatment is discontinued.

In addition, the compounds of the present invention can be co-administered or co-formulated with further active ingredients, such as anxiolytics, other agents which affect the levels of biogenic amines in the brain, such as nootropic agents, and tryptophan.

The present invention also provides a process for the preparation of compounds of structure (1) or pharmaceutically acceptable salts thereof, which process comprises reducing an amide of structure (2) or a compound of structure (4) in which R and R' are as defined above, and $R^3$ is hydroxy or $C_{1-4}$alkyl, and for compounds in which R" is other than hydrogen, N-alkylating the product with R"-X where X is chlorine, bromine, iodine, or other good leaving group easily displaced by a secondary amine, and optionally when R and/or R' are $C_{1-4}$alkyl alkylating the product with an alkyl halide, alkyl sulphate or other N-alkylating agent, and thereafter optionally forming a pharmaceutically acceptable salt.

Suitably the reduction of the amide (2) is carried out with lithium aluminium hydride or a similar reducing agent. Suitably this reduction is carried out in an inert solvent such as tetrahydrofuran.

Suitably the reduction of the compounds (4) can be carried out using sodium borohydride, lithium aluminium hydride, sodium in ethanol or liquid ammonia, or hydrogen and a catalyst such as platinum or palladium supported on charcoal.

Suitably the N-alkylation to produce compounds in which R" is other than hydrogen is carried out with a reagent R"-X in which X is bromine. Suitably the alkylation is carried out in the presence of a non-nucleophilic base, preferably tert-butylamine. Preferably an excess of the base is employed with respect to the stoichiometric quantity.

The amides of structure (2) can be prepared by reacting an acid of structure (3) with phosphorus pentachloride, phosphoryl chloride, thionyl chloride or similar halogenating agent, and reacting the product with an amine $R^1R^2NH$.

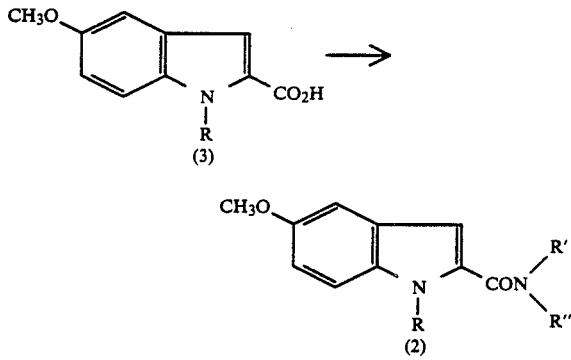

Preferably the halogenating agent is phosphorus pentachloride.

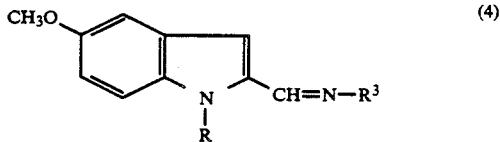

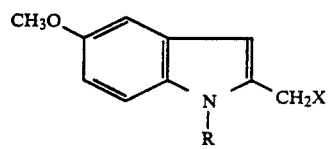

The compounds of structure (4) can be prepared by treating the corresponding aldehyde with hydroxylamine or an amine $R^3NH_2$.

An alternative process for preparing the compounds of structure (1) is to react a compound of structure (5) in which R is hydrogen or $C_{1-4}$alkyl, and X is a leaving group such as chlorine, bromine, iodine, alkylsulphonate such methanesulphonate, arylsulphonate such as p-toluenesulphonate, or tertiary ammonium such as trimethylammonium, with an amine of structure HNR'R" where R' and R" are as defined above.

In order to obtain the amines in which R" is other than hydrogen from the amines in which R is hydrogen, the latter were treated with the corresponding alkyl halide, preferably the corresponding bromide (R"-Br) in the theoretically required molar ratio, in a suitable solvent such as methanol, ethanol, diethyl ether, tetrahydrofuran, benzene or other similar substance, in the presence of at least one mole of tert-butylamine or preferably an excess, per mole of halide used. By means of chromatography, the resulting mixture of amines were separated. In cases where R' is methyl (R'=CH$_3$), the mixture only contains the amine (1) produced, with residues of the initial amine in which R" is hydrogen and traces of impurities. In cases where R' is hydrogen (R'=H), the mixtures contain the corresponding secondary amine (1) (R'=H and R"=propargyl, 2-butynyl or 2,3-butadienyl), small quantities (10–30%) of the tertiary amine (1) in which R'=R" (R"=propargyl, 2-butynyl or 2,3-butadienyl) and traces of impurities. These mixtures separated very well in all cases, the corresponding tertiary amine (1) R'=R" (R"=propargyl, 2-butynyl or 2,3-butadienyl), being the first eluted, followed by the corresponding secondary amine (1), with R'=H and R"=propargyl, 2-butynyl or 2,3-butadienyl, or of the corresponding tertiary amine (1), with R'=CH$_3$ and R"=propargyl, 2-butynyl or 2,3-butadienyl and, finally, with always greatly retarded elution, residues of the starting amine.

The present invention also provides a process for preparing N-methyl-5-methoxyindol-2-ylmethylamine and pharmaceutically acceptable salts thereof and pharmaceutical compositions for the treatment of depression which comprises this compound and a pharmaceutically acceptable carrier. The process and compositions are similar to those described herein with regard to compounds of structure (1) in which R and R" are hydrogen and R' is $C_2$–$C_4$alkyl.

The following table illustrates the structure of particular compounds of the invention (1). It also gives specific $pI_{50}$ values where $pI_{50} = -\log [I_{50}]$ where $[I_{50}]$ is the molar concentration of test compound which inhibits 50% of the in vitro activity of MAO from bovine brain mitochondria using tyramine as substrate.

| | | | Compounds of Structure (1) | Bovine Brain MAO | |
|---|---|---|---|---|---|
| | R | R' | R" | A  $pI_{50}$ | B |
| (a) | H | H | —CH$_2$—C≡CH | 6.66 | 3.96 |

-continued

Compounds of Structure (1)

| | R | R' | R'' | Bovine Brain MAO A | pI$_{50}$ | B |
|---|---|---|---|---|---|---|
| (b) | H | —CH$_2$—C≡CH | —CH$_2$—C≡CH | | | |
| (c) | H | CH$_3$ | —CH$_2$—C≡CH | 8.15 | | 6.35 |
| (d) | H | H | —CH$_2$—C≡C—CH$_3$ | 6.20 | | <3.48 |
| (e) | H | —CH$_2$—C≡C—CH$_3$ | —CH$_2$—C≡C—CH$_3$ | ≦4.70 | | <4.70 |
| (f) | H | CH$_3$ | —CH$_2$—C≡C—CH$_3$ | 8.05 | | 4.89 |
| (g) | H | H | —CH$_2$—CH=C=CH$_2$ | 7.35 | | 5.60 |
| (h) | H | —CH$_2$—CH=C=CH$_2$ | —CH$_2$—CH=C=CH$_2$ | 6.35 | ns | |
| (i) | H | CH$_3$ | —CH$_2$—CH=C=CH$_2$ | 7.75 | | 5.30 |
| (j) | CH$_3$ | H | —CH$_2$—C≡CH | 7.68 | | 4.35 |
| (k) | CH$_3$ | —CH$_2$—C≡CH | —CH$_2$—C≡CH | 5.55 | ns | |
| (l) | CH$_3$ | CH$_3$ | —CH$_2$—C≡CH | 8.05 | | 6.05 |
| (m) | CH$_3$ | H | —CH$_2$—C≡C—CH$_3$ | 6.89 | | 4.10 |
| (n) | CH$_3$ | —CH$_2$—C≡C—CH$_3$ | —CH$_2$—C≡C—CH$_3$ | 5.40 | | <3.30 |
| (o) | CH$_3$ | CH$_3$ | —CH$_2$—C≡C—CH$_3$ | 7.45 | ns | |
| (p) | CH$_3$ | H | —CH$_2$—CH=C=CH$_2$ | 7.66 | | 6.40 |
| (q) | CH$_3$ | —CH$_2$—CH=C=CH$_2$ | —CH$_2$—CH=C=CH$_2$ | 6.52 | ns | |
| (r) | CH$_3$ | CH$_3$ | —CH$_2$—CH=C=CH$_2$ | 8.27 | | 6.30 |
| (s) | H | H | H | 4.30 | ns | |
| (t) | H | CH$_3$ | H | ≦4.00 | | <4.00 |
| (u) | CH$_3$ | H | H | 4.74 | ns | |
| (v) | CH$_3$ | CH$_3$ | H | 3.89 | ns | | ns = non-selective

The following examples illustrate the invention. Temperatures are recorded in degrees centigrade.

PREPARATION OF 2-(5-METHOXYINDOLE)CARBOXAMIDES OF STRUCTURE 2

Preparation

To a solution of 1-methyl-5-methoxyindole-2carboxylic acid (4.1 g; 20 mmoles) in ethyl ether (250 ml) and benzene (200 ml), dried over sodium, phosphorus pentachloride (5.0 g, 24 mmoles) was added in small portions with agitation. The mixture was stirred at ambient temperature overnight, protected from humidity. The solvent was removed under vacuum by rotary evaporation and to the residue was added a fresh portion of dry solvent (35 ml), evaporation in a vacuum being performed again. This operation was repeated several times until all the hydrogen chloride and phosphorus oxychloride had been eliminated. The residue of the crude acid chloride was dissolved in dry ether or dry benzene, the solution chilled in an ice-bath and, with agitation, 40% aqueous methylamine solution (5.0 g) was added. The mixture was agitated afterwards at ambient temperature overnight. The solvent was removed under vacuum in a rotary evaporator and the residue was suspended in water. The insoluble material was collected by filtration and recrystallised; melting point=183° C. (ethanol). Quantitative yield.

In a similar manner, the following compounds were obtained:

2-(5-methoxyindole)carboxamide, Starting from 5-methoxyindole-2-carboxylic acid and ammonium hydroxide; m.p.=205°-206° C. (ethanol/water). Quantitative yield. N-methyl-2-(5-methoxyindole)carboxamide. Starting from 5-methoxyindole-2-carboxylic acid and methyl amine; m.p. =226°-228° C. (ethanol). Quantitative yield. 2-(1-.methyl-5-methoxyindole)carboxamide. From 1-methyl-5-methoxyindole-2-carboxylic acid and ammonium hydroxide; m.p.=220° C. (ethanol). Quantitative yield.

Preparation of 2-(5-methoxy-indolyl)methylamines Structure 1 R''=H.

EXAMPLE 1

N-methyl-2-(1-methyl-5-methoxy-indolyl)methylamine, 1v

To a suspension of lithium aluminium hydride (3.0 g, 70 mmoles) in tetrahydrofuran (100 ml), dried over sodium, was added dropwise a solution of N-methyl-2-(1-methyl-5methoxyindole)carboxamide (4.10 g, 20 mmoles) in tetrahydrofuran (60 ml). The mixture was heated to reflux until reduction of the amide was complete (about 5 hours) and afterwards it was chilled in an ice-bath. Under agitation, water was added drop by drop until there was complete destruction of the excess hydride. The aluminium hydroxide precipitate was centrifuged and the supernatant was decanted. The precipitate was extracted several times with tetrahydrofuran. The combined extracts were brought to a state of dryness by rotary evaporation to yield the crude amine !v which was virtually pure: m.p.=55° C. (benzene/petroleum ether). Yield 93-98%.

The hydrochloride of the amine was obtained by dissolving the latter in dry ether, chilling the solution and adding hydrogen chloride solution in absolute ethanol; m.p.=226° C. (ethanol/water).

The following compounds were obtained in a similar way:

2-(5-methoxy-indolyl)methylamine, 1s.
m.p.=85° C. (hexane). Yield 92-96%. Hydrochloride, m.p.>295° C. (absolute ethanol/ether).

N-methyl-2-(5-methoxy-indolyl)methylamine, 1t. The amine was obtained in the form of an oil, with a yield of 96%.

Hydrochloride. m.p.=212° C. (ethanol/ether). 2-(1-methyl-5-methoxy-indolyl)methylamine. 1u. m.p.=64° C. (benzene/petroleum ether).

Yield around 96%.

Hydrochloride, m.p.>250° C. (ethanol/ether).

EXAMPLE 2

N-(2,3-butadienyl)-2-(1-methyl-5-methoxy-indolyl)methylamine, 1p and

N,N-bis(2,3-butadienyl)-2-(1-methyl-5-methoxy-indolyl)methylamine, 1q.

From the free amine 1u, its hydrochloride or another salt, the following were obtained by treatment with 2,3-butadienyl bromide, according to the following alternative processes:

1. Starting from the free amine. To a solution of the amine 1u (1.54 g, 7.5 mmoles) in tetrahydrofuran (about 50 ml), was added tert-butylamine (0.8 g, 11 mmoles) and to the cold solution was added, dropwise with agitation, 2,3-butadienyl bromide (0.10 g, 7.5 mmoles) dissolved in tetrahydrofuran (5 ml). The mixture was agitated at ambient temperature for about 24 hours, in which thin layer chromatography of an aliquot specimen indicated that the reaction was perfectly complete. The solvent was removed under vacuum by rotary evaporation, and the residue was dissolved in water. The basic solution (if it is not such a solution, it is alkalinised with sodium hydroxide, sodium bicarbonate or sodium carbonate), followed by extraction with ether and the combined extracts are dried over anhydrous sodium sulphate. The solution is concentrated under vacuum in a rotary evaporator and applied to a dry column (20×4 cm) of Merck 60 F-245 silica gel. The column was eluted with a mixture of ethyl ether and toluene (10/1, v/v). The composition of the eluates was examined by thin layer chromatography, developed by the same solvent. First to be eluted was the compound 1q (Rf=0.82), followed by the compound 1p (Rf=0.38) and subsequently residues of the initial amine were eluted. The eluates containing each of the residues were dissolved in ethyl ether and the respective solutions were treated with a solution of hydrogen chloride in absolute ethanol, and the respective hydrochlorides crystallised. Thus were obtained: the hydrochloride of 1p, m.p.=204° C. (ethanol); yield around 55%; the hydrochloride of 1q, m.p.=172° C. (ethanol/ether), yield around 20%.

2 Starting from the hydrochloride of 1u. Carrying out one of the following two methods:

a) The hydrochloride of 1u is dissolved in water. The solution is alkalinised with a solution of sodium hydroxide, sodium bicarbonate or carbonate. The amine 1u is extracted with ether and the combined extracts are dried with anhydrous sodium sulphate. The solvent is eliminated and the residue of the free amine treated as indicated earlier under point 1.

b) The hydrochloride of 1u is suspended in tetrahydrofuran and at least three moles of tertiary butylamine per mole of hydrochloride are added to the suspension. The mixture is agitated at ambient temperature for one hour and then chilled in an ice-bath, the next stage being to add 2,3-butadienyl bromide as indicated earlier in para. 1.

By either of the methods indicated, the yields of amines 1p and 1q depend upon the molar ratio of amine 1u used to 2-butadienyl bromide. If two moles of bromide per mole of amine are used, then the yields are virtually reversed compared with those stated, around 20–25% of the amine 1p and 55–60% of the amine 1q being obtained.

Following at least one of the above-mentioned processes and using a molar ratio of starting amine to alkyl halide of 1:1, the following compounds were similarly obtained:

N-propargyl-2-(5-methoxy-indolyl)methylamine, 1a. From the amine 1s and propargyl bromide. Chromatography eluent, ethyl ether; Rf=0.25. Hydrochloride, m.p. 183° C. (ethanol/ether). Yield around 50%. N,N-bis(propargyl)-2-(5-methoxy-indolyl)methylamine, 1b. From the amine 1s and propargyl bromide. Chromatography eluent, ethyl ether, Rf=0.79. Hydrochloride, unstable. Yield around 15 to 20%.

N-methyl-N-propargyl-2-(5-methoxy-indolyl)methylamine, 1c. From the amine 1t and propargyl bromide. Chromatography eluent, ethyl ether; Rf=0.75. Yield around 75%. Acid oxalate, m.p.=118° C. (ethanol).

N-(2-butynyl)-2-(5-methoxy-indolyl)methylamine, 1d. From amine 1s and 2-butynyl bromide. Chromatography solvent, ethyl ether, Rf=0.40. Yield around 50%. Acid oxalate m.p.=190° C. (ethanol).

N,N-bis(2-butynyl)-2-(5-methoxy-indolyl)methylamine, 1e. Starting from the amine 1s and 2-butynyl bromide. Chromatography solvent, ethyl ether, Rf=0.82. Yield, 20%. Acid oxalate, m.p.=159° C. (ethanol/ethyl ether).

N-(2-butynyl)-N-methyl-2-(5-methoxy-indolyl)methylamine. 1f. From amine 1t and 2-butynyl bromide. Chromatography solvent, ethyl ether, Rf=0.45. Yield around 75%. Acid oxalate, m.p.=170° C. (ethanol/ether).

N-(2,3-butadienyl)-2-(5-methoxy-indolyl)methylamine, 1g. From amine 1s and 2,3-butadienyl bromide. Chromatography solvent, ethyl ether/methanol (2/1, v/v), Rf=0.49. Yield around 55%. Acid oxalate. m.p.=168° C. (methanol).

N,N-bis(2,3-butadienyl)-2-(5-methoxy-indolyl)methylamine, 1h. From amine 1s and 2,3-butadienyl bromide. Chromatography solvent, ethyl ether/methanol (2/1, v/v), Rf=0.71. Yield around 15%. Acid oxalate, m.p.=130° C. (ethanol/ethyl ether).

N-(2,3-butadienyl)-N-methyl-2-(5-methoxy-indolyl)methylamine, 1i. From amine 1t and 2,3-butadienyl bromide. Chromatography solvent, ethyl ether, Rf=0.75. Yield around 75–80%. Acid oxalate, m.p.=52° C. (ethanol/ether).

N-propargyl-2-(1-methyl-5-methoxy-indolyl)methylamine. 1j. From amine 1u and propargyl bromide. Chromatography solvent, ethyl ether/benzene (10/1, v/v), Rf=0.42. Yield around 45–50%. Hydrochloride. m.p.=205° C. (ethanol/ether).

N,N-bis(propargyl)-2-(1-methyl-5-methoxy-indolyl)methylamine, 1k. From the amine 1u and propargyl bromide. Chromatography solvent, ethyl ether/benzene (10/1, v/v), Rf=0.78. Yield around 15 to 20%.

N-methyl-N-propargyl-2-(1-methyl-5-methoxy-indolyl)methylamine, 1l. From the amine 1v and propargyl bromide. Chromatography solvent, ethyl ether, Rf=0.45. Yield around 75%. Hydrochloride. m.p.=188° C. (ethanol/ether). N-(2-butynyl)-2-(1-methyl-5-methoxy-indolyl)methylamine, 1m. From the amine 1u and 2-butynyl bromide. Chromatography solvent, ethyl ether/toluene (10/1, v/v), Rf=0.42. Yield around 50%. Hydrochloride, m.p.=210° C. (ethanol).

N,N-bis(2-butynyl)-2-(1-methyl-5-methoxy-indolyl)methylamine, 1n. From the amine 1u and 2-butynyl bromide. Chromatography solvent, ethyl ether/toluene (10/1, v.v). Rf=0.87. Yield around 10–15%. Hydrochloride, m.p.=117° C. (ethanol/ether).

N-(2-butynyl)-N-methyl-2-(1-methyl-5-methoxy-indolyl)methylamine, 1o. From the amine 1v and 2-butynyl bromide. Chromatography solvent, ethyl ether/benzene (3/1, v/v), Rf=0.40. Yield 75%. Hydrochloride, m.p.=199° C. (ethanol).

N-(2,3-butadienyl)-N-methyl-2-(1-methyl-5-methoxy-indolyl)-methylamine, 1r. From the amine 1v and 2,3-butadienyl bromide. Solvent for chromatography, ethyl ether/benzene (1/1, v/v), Rf=0.47. Yield around 78%. Hydrochloride, m.p.=185° C. (ethanol).

All the compounds mentioned in the examples gave a correct elemental analysis for C, H, N and, where applicable, Cl, and also IR, UV and $^1$H-NMR spectra were satisfactory with regard to what was expected for the suggested structures.

Preparation of pharmaceutical composition.

EXAMPLE A

A tablet for oral administration is prepared by combining

|  | Mg/Tablet |
|---|---|
| Compound of structure (1) | 100 |
| lactose | 153 |
| Starch | 33 |
| crospovidone | 12 |
| microcrystalline cellulose | 30 |
| magnesium stearate | 2 |
|  | 330 mg | into a 9 mm tablet.

We claim:
1. A compound of structure (1):

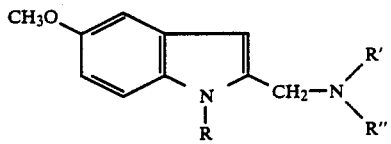

or a pharmaceutically acceptable salt thereof, wherein
R is hydrogen or $C_{1-4}$alkyl,
R' is hydrogen, $C_{1-4}$alkyl, or a $C_{1-4}$alkyl group substituted by an alkyne or allene group, provided that R' is not methyl when R and R" are both hydrogen, and
R" is hydrogen or a $C_{1-4}$alkyl group substituted by an alkyne or allene group.

2. A compound according to claim 1 wherein R is hydrogen or methyl.
3. A compound according to claim 1 or claim 2 wherein R' is propargyl, 2-butynyl, 2,3-butadienyl, hydrogen or methyl.
4. A compound according to claim 3 wherein R" is hydrogen, propargyl, 2-butynyl or 2,3-butadienyl.
5. A compound according to any one of claim 4 wherein R is methyl.
6. A compound according to any one of claim 5 wherein R' is methyl or R' and R" are both hydrogen.
7. A compound according to claim 6 wherein R" is propargyl or 2-butynyl.
8. A compound according to claim 1 which is:
N-methyl-N-propargyl-2-[1-methyl-5-methoxyindolyl]-methylamine
N-propargyl-2-[1-methyl-5-methoxyindolyl]methylamine
N-(2-butynyl)-2-[1-methyl-5-methoxyindolyl]methylamine
N-(2-butynyl)-N-methyl-2-[1-methyl-5-methylamine
N-(2,3-butadienyl)-2-[1-methyl-5-methoxyindolyl]methylamine
N-(2,3-butadienyl)-N-methyl-2-[1-methyl-5-methoxyindolyl]methylamine, or
5-methoxyindol-2-ylmethylamine or a· pharmaceutically acceptable acid addition salt thereof.

9. A pharmaceutical composition which comprises a compound according to claim 1 and a pharmaceutically acceptable carrier.
10. A method of treatment of depressive diseases in a mammal, which method comprises administering to said mammal a non-toxic but effective indole derivative as claimed in claim 1.
11. A compound according to claim 8 which is N-methyl-N-propargyl-2-[1-methyl-5-methoxyindolyl]-methylamine.
12. A pharmaceutical composition which comprises a compound according to claim 8 and a pharmaceutically acceptable carrier.
13. A pharmaceutical composition of claim 12 wherein the compound is N-methyl-N-propargyl-2-[1-methyl-5-methocyindolyl] methylamine.

* * * * *

UNITED STATES PATENT AND TRADEMARK OFFICE
CERTIFICATE OF CORRECTION

PATENT NO. : 5,130,327
DATED : July 14, 1992
INVENTOR(S) : Alvarez et al.

It is certified that error appears in the above-identified patent and that said Letters Patent is hereby corrected as shown below:

Column 14, lines 10-11,

Claim 5 should read: "A compound according to Claim 4 wherein R is methyl."
Column 14, lines 12-13, Claim 6 should read: "A compound according to Claim 5 wherein R' is methyl or R' and R" are both hydrogen."

Signed and Sealed this

Fifth Day of October, 1993

BRUCE LEHMAN

*Attest:*

*Attesting Officer*   *Commissioner of Patents and Trademarks*